United States Patent
Yamada et al.

(10) Patent No.: US 8,841,817 B2
(45) Date of Patent: Sep. 23, 2014

(54) SURFACE ACOUSTIC WAVE SENSOR

(75) Inventors: Hideaki Yamada, Kariya (JP); Kazuhiko Kano, Toyoake (JP)

(73) Assignee: DENSO CORPORATION, Kariya (JP)

( * ) Notice: Subject to any disclaimer, the term of this patent is extended or adjusted under 35 U.S.C. 154(b) by 251 days.

(21) Appl. No.: 13/557,378

(22) Filed: Jul. 25, 2012

(65) Prior Publication Data

US 2013/0026882 A1 Jan. 31, 2013

(30) Foreign Application Priority Data

Jul. 27, 2011 (JP) ................. 2011-164507

(51) Int. Cl.
*H03H 9/02* (2006.01)
*H01L 41/113* (2006.01)
*H03H 9/05* (2006.01)
*G01N 29/24* (2006.01)
*G01N 29/38* (2006.01)
*G01N 29/42* (2006.01)

(52) U.S. Cl.
CPC ........... *H01L 41/1132* (2013.01); *H03H 9/058* (2013.01); *H03H 9/02622* (2013.01); *H03H 9/0585* (2013.01); *G01N 29/2462* (2013.01); *G01N 29/38* (2013.01); *G01N 29/42* (2013.01); *G01N 2291/0423* (2013.01)
USPC .................................... 310/313 R

(58) Field of Classification Search
CPC ........... H01L 41/1132; H03H 9/02535; H03H 9/02614; H03H 9/02622; H03H 9/02629; H03H 9/05; H03H 9/058; H03H 9/0585
USPC ....... 310/313 R, 313 A, 313 B, 313 C, 313 D
See application file for complete search history.

(56) References Cited

U.S. PATENT DOCUMENTS

| | | | |
|---|---|---|---|
| 5,874,266 | A | 2/1999 | Palsson |
| 6,236,141 | B1 | 5/2001 | Sato et al. |
| 2004/0041496 | A1 * | 3/2004 | Imai et al. ............... 310/313 D |
| 2009/0133504 | A1 | 5/2009 | Kalinin |

FOREIGN PATENT DOCUMENTS

| | | |
|---|---|---|
| JP | 57-029916 A | 2/1982 |
| JP | A-02-65406 | 3/1990 |
| JP | A-06-177701 | 6/1994 |
| JP | 08-145614 A | 6/1996 |
| JP | A-2002-26688 | 1/2002 |
| JP | 2006-258733 A | 9/2006 |
| JP | 2008-541121 A | 11/2008 |
| JP | A-2008-275503 | 11/2008 |
| JP | A-2008-309779 | 12/2008 |
| JP | A-2009-109261 | 5/2009 |

* cited by examiner

*Primary Examiner* — Derek Rosenau
(74) *Attorney, Agent, or Firm* — Posz Law Group, PLC

(57) ABSTRACT

In a SAW device, a first area placed at a surface of a measurement subject directly under a propagation portion is fixed to the measurement subject, and a second area placed at the surface of the measurement subject directly under both a drive electrode and a reflector is not fixed to the measurement subject. When a strain is generated in the measurement subject, a strain is generated only in the propagation portion, and a phase change is generated in a surface acoustic wave reflected by the reflector. Because the phase change is hardly affected by a temperature change, the strain of the measurement subject can be measured based on the phase change. Because a resonant frequency of the SAW device is changed by the temperature change, but is not affected by the strain of the measurement subject, a temperature can be measured based on a resonant frequency change.

9 Claims, 9 Drawing Sheets

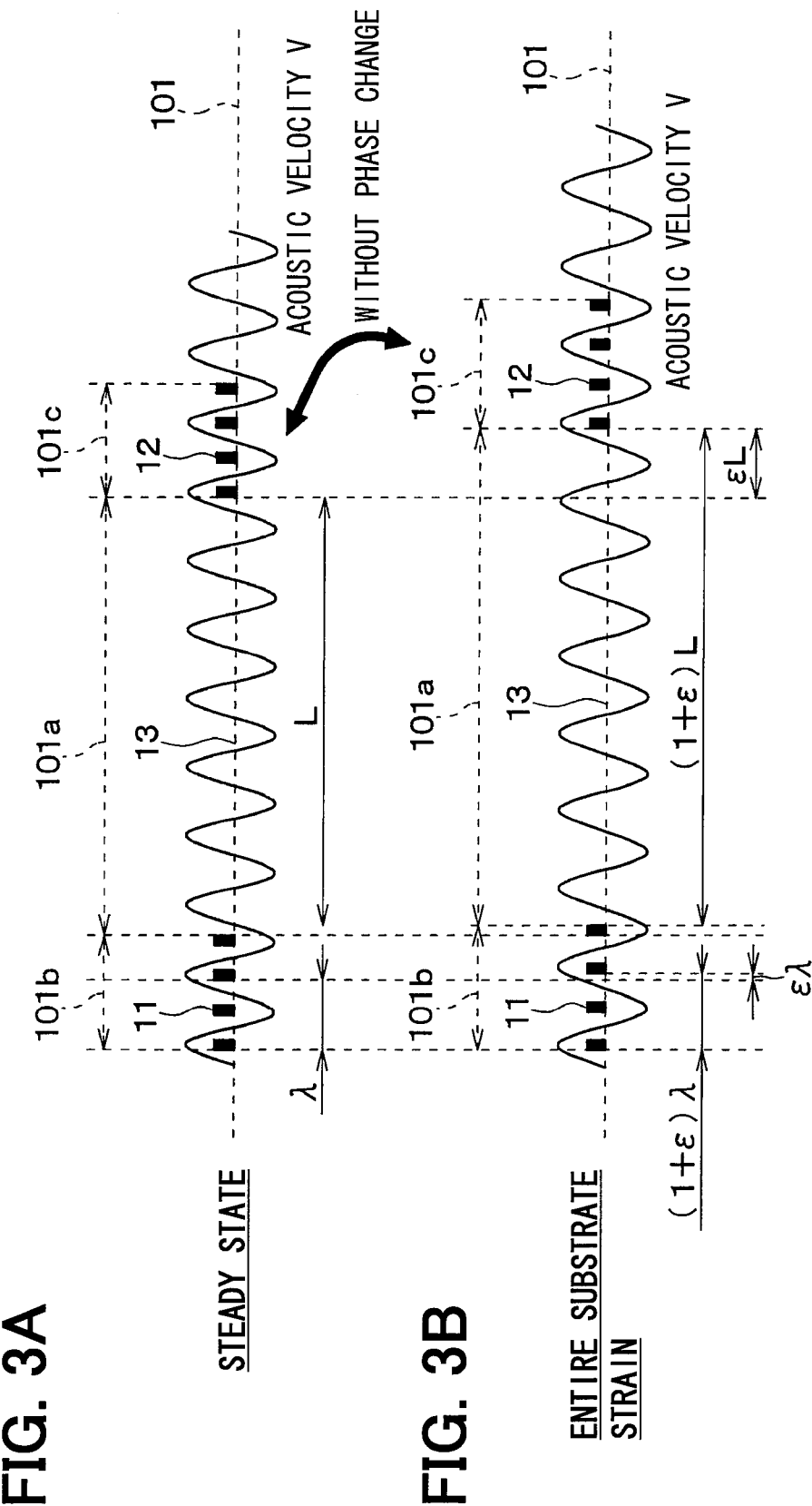

STEADY STATE

ONLY TEMPERATURE CHANGE

TEMPERATURE CHANGE + PROPAGATION STRAIN

US 8,841,817 B2

SURFACE ACOUSTIC WAVE SENSOR

CROSS REFERENCE TO RELATED APPLICATION

This application is based on Japanese Patent Application No. 2011-164507 filed on Jul. 27, 2011, the contents of which are incorporated herein by reference in its entirety.

TECHNICAL FIELD

The present disclosure relates to a surface acoustic wave sensor which detects a physical quantity using a surface acoustic wave (SAW).

BACKGROUND

As two detection methods of a surface acoustic wave sensor, there are a phase detection method (for example, refers to Patent Documents 1 to 5) and an oscillation method (for example, refers to Patent Document 6).

The surface acoustic wave sensor of the phase detection method, for example, includes a surface acoustic wave (SAW) device, an oscillation circuit, and a phase detection circuit. The SAW device, for example, includes a piezoelectric substrate, a drive electrode (IDT pair) and a reflector. The drive electrode and the reflector are arranged at a surface of the piezoelectric substrate.

A measurement principle of the surface acoustic wave sensor of the phase detection method is as the following. When an excitation signal (burst signal) corresponding to a resonant frequency of the drive electrode is transmitted from the oscillation circuit, an electrical signal is converted to a mechanical oscillation by the drive electrode. Then, a SAW is excited on the surface of the piezoelectric substrate. The SAW excited by the drive electrode is transmitted along a propagation portion on the surface of the piezoelectric substrate, and is reflected by the reflector. The reflected SAW is converted to an electrical signal by the drive electrode, and the converted electrical signal is outputted toward the phase detection circuit. In a case where the signal inputted from the SAW device to the phase detection circuit is compared to the signal directly inputted from the oscillation circuit to the phase detection circuit when the SAW is excited, a phase of the SAW outputted from the SAW device is changed by an electrical or mechanical characteristic change of the propagation portion. Therefore, a physical quantity to be measured can be detected by the phase.

The surface acoustic wave sensor of the phase detection method may be used as a gas sensor (for example, refers to Patent Documents 1, 2), a liquid density sensor (for example, refers to Patent Document 3), a liquid characteristic sensor (for example, refers to Patent Document 4), or a cell characteristic detection device (for example, refers to Patent Document 5).

In the gas sensor, a gas sensitive membrane is arranged at the propagation portion so as to sense a gas. When the gas sensitive membrane is a selective membrane, a mass effect is generated because the gas is adsorbed by the membrane. Therefore, a gas density can be detected according to a propagation characteristic change of the SAW. In the liquid characteristic sensor, a liquid is spread on the propagation portion so as to sense a liquid characteristic. When the liquid is spread on the propagation portion, because a phase and amplitude of the SAW are changed by a conductivity of the liquid, a permittivity of the liquid, a mass of the liquid, and a viscosity of the liquid, the liquid characteristic can be detected.

The surface acoustic wave sensor of the oscillation method includes the SAW device and the oscillation circuit. The physical quantity is detected according to an oscillation frequency (resonant frequency of the SAW device) change oscillated in the oscillation circuit. For example, when a strain is generated in the propagation portion of the SAW device, the resonant frequency of the SAW device is changed according to the strain generated in the propagation portion. Therefore, the strain generated in the SAW device can be measured from the resonant frequency change.

In the surface acoustic wave sensor of the oscillation method, the resonant frequency of the SAW is significantly changed according to a temperature change. Therefore, at least two SAW devices are used so as to reduce the resonant frequency change generated by the temperature change (for example, refers to Patent Document 6).

[Prior Art Documents]
 [Patent Document 1] JP-A-2002-26688
 [Patent Document 2] JP-A-2009-109261
 [Patent Document 3] JP-A-2008-275503
 [Patent Document 4] JP-A-2008-309779
 [Patent Document 5] JP-A-2010-29193
 [Patent Document 6] JP-A-2008-541121

SUMMARY

In the conventional sensor of the phase detection method, a strain and a temperature can not be measured when a frequency of an excited surface acoustic wave (SAW) is changed in a case where a resonant frequency generated by the strain of the drive electrode is changed.

When a temperature of a measurement subject and a strain of the measurement subject are transmitted to a SAW device, a strain (expansion or contraction) is generated equally not only at the propagation portion but also at the drive electrode and the reflector.

On the other hand, in the conventional sensor of the oscillation method, the strain generated in the SAW device can be measured as the above description.

However, in the conventional sensor of the oscillation method, because the resonant frequency of the SAW is changed by both the strain generated in the SAW device and a temperature change of the SAW device, at least two SAW devices have to be used so as to reduce the resonant frequency generated by the temperature change. For example, a first SAW device is arranged at a position where the first SAW device only receives the temperature change, a second SAW device is arranged at a position where the second SAW device receives both the temperature change and the strain.

Because at least two SAW devices are used, mounting positions of the SAW devices and mounting procedures of the SAW devices may become complicate, and a signal processing circuit may become complicate.

It is an object of the present disclosure to provide a SAW sensor, which can measure both the strain and the temperature by a single SAW device.

According to a first aspect of the present disclosure, the SAW sensor includes a substrate, a first electrode, a second electrode, a propagation portion, a phase detection device and a frequency detection device. The substrate is arranged at a surface of a measurement subject which is a measuring object of both the strain and the temperature. At least a part of the substrate may be made of a piezoelectric material. The first electrode is arranged at a top surface of the substrate. The first electrode oscillates or receives the SAW. The second electrode is also arranged at the top surface of the substrate. The second electrode receives or reflects the SAW oscillated by the first electrode. The propagation portion is placed at the top surface of the substrate between the first electrode and the second electrode. The propagation portion transmits the SAW from the first electrode toward the second electrode. The phase detection device detects a phase of the SAW oscillated by the first electrode and a phase of the SAW received or reflected by the second electrode. The frequency detection device detects a resonant frequency of the first electrode.

A first area, which is placed at a bottom surface of the substrate directly under the propagation portion, is fixed to the measurement subject. A second area, which is placed at the bottom surface of the substrate directly under both the first electrode and the second electrode, is not fixed to the measurement subject.

Between the areas of the bottom surface of the substrate placed directly under the first and the second electrodes and the propagation portion, only the first area placed directly under the propagation portion is bonded to the measurement subject. When the strain is generated in the measurement subject, the strain of the measurement subject is only transmitted to the propagation portion. Because the first area of the substrate fixed to the measurement subject is bonded to the measurement subject, the first area is deformed corresponding to a deformation of the measurement subject. Because the second area of the substrate not fixed to the measurement subject is not bonded to the measurement subject, the second area is not deformed.

Therefore, when the strain is generated in the measurement subject, the strain is generated only in the propagation portion, and thereby a phase change is generated in the SAW received or reflected by the second electrode with respect to a phase of the SAW oscillated by the first electrode. The phase change is hardly affected by a temperature change of the measurement subject, because a temperature change is generated equally in the first electrode, the second electrode and the propagation portion, when the temperature of the measurement subject is changed.

Thus, the strain of the measurement subject can be measured based on the phase change of the SAW detected by the phase detection device. Besides, the SAW is received or reflected by the second electrode.

When the temperature of the measurement subject is changed, an acoustic velocity of the SAW is changed. Because an interval between electrodes of the first electrode is expanded (contracted) by the temperature change, the resonant frequency of the first electrode is changed when the SAW is excited. When the strain is generated in the measurement subject, the strain is only generated in the propagation portion, and the strain of the propagation portion does not affect the resonant frequency. In this case, the resonant frequency change is not affected by the strain of the measurement subject.

The temperature of the measurement subject can be measured based on the resonant frequency change detected by the frequency detection device. Therefore, both the strain and the temperature can be measured by the single SAW device.

BRIEF DESCRIPTION OF THE DRAWINGS

The above and other objects and advantages of the present disclosure will be more readily apparent from the following detailed description made with reference to the accompanying drawings. In the drawings:

FIG. 3A is a schematic diagram showing a SAW of the SAW device in a steady state, and FIG. 3B is a schematic diagram showing a SAW of the SAW device in a strain state of an entire substrate, according to the first comparison example;

DETAILED DESCRIPTION

Figure 1A:
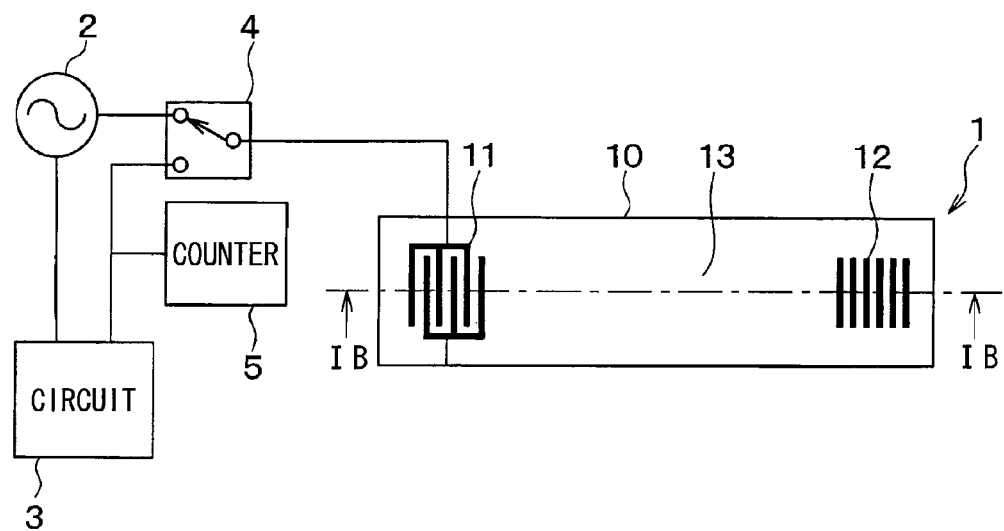
FIG. 1A is a schematic diagram showing an entire structure of a surface acoustic wave (SAW) sensor according to a first embodiment of the present disclosure.

Embodiments of the present disclosure will be described hereafter referring to drawings. In the embodiments, a part that corresponds to a matter described in a preceding embodiment may be assigned with the same reference numeral, and redundant explanation for the part may be omitted. When only a part of a configuration is described in an embodiment, another preceding embodiment may be applied to the other parts of the configuration. The parts may be combined even if it is not explicitly described that the parts can be combined. The embodiments may be partially combined even if it is not explicitly described that the embodiments can be combined, provided there is no harm in the combination.

(First Embodiment)

As shown in FIG. 1A, a sensor of a first embodiment includes a SAW device 1, an oscillation circuit 2, a phase detection circuit 3, a switch 4 and a frequency counter 5.

The SAW device 1 includes a substrate 10, a drive electrode 11 and a reflector 12. The SAW device 1 is an element using a SAW. The drive electrode 11 and the reflector 12 are arranged at a surface of the substrate 10.

The substrate 10 is a piezoelectric substrate. An entire piezoelectric substrate is formed by a piezoelectric material. A piezoelectric substrate formed by a common piezoelectric material can be used as the substrate 10.

The drive electrode 11 is a first electrode oscillates (excites) or receives the SAW. In the drive electrode 11, a pair of comb electrodes faces to each other, and teeth of each comb electrodes are arranged alternately with each other.

The reflector 12 is a second electrode which reflects the SAW oscillated by the drive electrode 11. In the reflector 12, several linear electrodes are arranged in parallel.

The oscillation circuit 2 is a circuit for exciting the SAW in the SAW device 1. The oscillation circuit 2 transmits an excitation signal (burst signal) to the drive electrode 11. A common circuit can be used as the oscillation circuit 2.

The phase detection circuit 3 is a phase detection device detecting a phase of the SAW excited by the drive electrode 11 and a phase of the SAW reflected by the reflector 12. A first signal from the oscillation circuit 2 is inputted to the phase detection circuit 3. At the same time, a second signal of the SAW outputted from the SAW device 1 is inputted to the phase detection circuit 3 via the switch 4. A common circuit can be used as the phase detection circuit 3.

The switch 4 is a switching device for switching to a first steady state or a second steady state. In the first steady state, the switch 4 switches to electrically connect with the oscillation circuit 2 and the SAW device 1. In the second steady state, the switch 4 switches to electrically connect with the phase detection circuit 3 and the SAW device 1.

The frequency counter 5 is a frequency detection device detecting a frequency of the SAW. The frequency of the SAW corresponds to a resonant frequency of the SAW device 1. In the first embodiment, the frequency counter 5 measures the frequency of the SAW outputted from the SAW device 1 at a specified time interval.

Figure 1B:
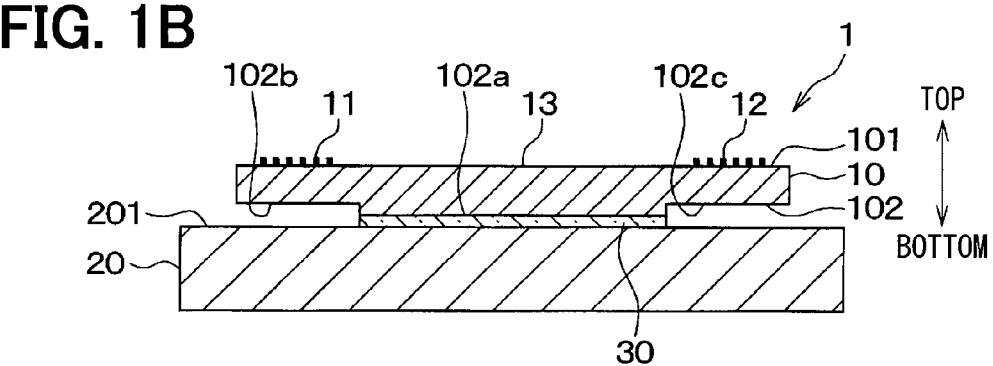
FIG. 1B is a sectional view taken along the line IB-IB of a SAW device of the SAW sensor in FIG. 1A.

As shown in FIG. 1B, the SAW device 1 is arranged at a surface 201 of the measurement subject 20. The measurement subject 20 is a measuring object of a strain and a temperature. For example, when the sensor measures a pressure, the measurement subject is a metal diaphragm portion strained by the pressure.

As an arrow of the FIG. 1B, with respect to the surface 201 of the measurement subject 20, one end close to the surface 201 corresponds to a down direction, another end far away from the surface 201 corresponds to an up direction. Then, in the substrate 10 of the SAW device 1, a surface close to the surface 201 of the measurement subject 20 corresponds to a bottom surface 102, and another surface far away from the surface 201 of the measurement subject 20 corresponds to a top surface 101.

The drive electrode 11 and the reflector 12 are arranged at the top surface 101 of the substrate 10. In the top surface 101 of the substrate 10, a propagation portion 13 is arranged between the drive electrode 11 and the reflector 12. The propagation portion 13 is an area where the SAW is transmitted from the drive electrode 11 toward the reflector 12. Besides, the propagation portion 13 does not include an area where the drive electrode 11 and the reflector 12 are arranged at. That is, the propagation portion 13 is an area of the top surface 101 of the substrate 10 except the area where the drive electrode 11 and the reflector 12 are arranged at.

In the substrate 10, an area 102a placed at the bottom surface 102 directly under the propagation portion 13 is fixed to the surface 201 of the measurement subject 20. In the substrate 10, an area 102b, placed at the bottom surface 102 directly under the drive electrode 11, and an area 102c, placed at the bottom surface 102 directly under the reflector 12, are not fixed to the surface 201 of the measurement subject 20.

Specifically, the substrate 10 is shaped that the areas 102b, 102c placed at the bottom surface 102 directly under the drive electrode 11 and the reflector 12 are more recessed than the area 102a placed at the bottom surface 102 directly under the propagation portion 13. As shown in FIG. 1B, a cross-section of the substrate 10 is a T-shape. With respect to a substrate 10 in which the whole bottom surface 102 is flat, the T-shape can be obtained by a generally used etching method as a semiconductor manufacturing technology to remove the areas 102b, 102c.

The area 102a placed at the bottom surface 102 directly under the propagation portion 13 is bonded to the surface 201 of the measurement subject 20 by a bonding material 30. For example, a low melting glass or an adhesive can be used as the bonding material 30.

The areas 102b, 102c placed at the bottom surface 102 directly under the drive electrode 11 and the reflector 12 face to the surface 201 of the measurement subject 20 via a space. The whole surface 201 of the measurement subject 20 opposite to the substrate 10 is a flat surface.

In the first embodiment, a structure, in which only the area 102a placed at the bottom surface 102 directly under the propagation portion 13 is fixed to the surface 201 of the measurement subject 20, can be obtained according to the shape of the substrate 10 without adding any other parts.

In the substrate 10 formed as the above shape, when the bonding material 30 is arranged just above the surface 201 of the measurement subject 20, and when the substrate 10 is arranged just above the bonding material 30, the SAW device 1 and the measurement subject 20 can be bonded.

In the sensor of the first embodiment, only the area 102a placed at the bottom surface 102 directly under the propagation portion 13 is fixed to the surface 201 of the measurement subject 20. When the strain of the measurement subject 20 is transmitted to the SAW device 1, a strain is generated only in the propagation portion 13 of the top surface 101. The phase of the SAW reflected by the reflector 12 is changed with respect to a phase of the SAW excited by the drive electrode 11. In the sensor of the first embodiment, the strain of the measurement subject 20 is measured according to the phase change of the SAW reflected by the reflector 12.

Specifically, the switch 4 switches to the first steady state, that is, the switch 4 is electrically connected with the oscillation circuit 2 and the drive electrode 11. In the first steady state, when the excitation signal corresponding to the resonant frequency of the drive electrode 11 is transmitted from the oscillation circuit 2 to the drive electrode 11, the SAW is excited on the surface of the substrate 10 by the drive electrode 11. At the same time, an electrical signal is also transmitted from the oscillation circuit 2 toward the phase detection circuit 3. The SAW excited in the drive electrode 11 is transmitted through the propagation portion 13, and then is reflected by the reflector 12, and then is received by the drive electrode 11. Then, the switch 4 switches to the second steady state, that is, the switch 4 is electrically connected with the phase detection circuit 3 and the drive electrode 11. In the second steady state, the SAW reflected by the reflector 12 is converted to an electrical signal at the drive electrode 11, and the converted electrical signal is outputted toward the phase detection circuit 3. Based on both the signal inputted from the oscillation circuit 2 to the phase detection circuit 3 and the signal inputted from the drive electrode 11 to the phase detection circuit 3, a phase change amount of the SAW reflected by the reflector 12 with respect to the phase of the SAW excited by the drive electrode 11 can be detected. Therefore, the strain of the measurement subject 20 can be measured.

When a temperature change is generated in the SAW device 1, the resonant frequency of the SAW excited in the drive electrode 11 is changed. In the sensor of the first embodiment, based on a comparison between a frequency detected by the frequency counter 5 and a standard frequency of a specified temperature, or a comparison among several frequencies detected by the frequency counter 5, a resonant frequency change amount of the SAW excited in the drive electrode 11 can be detected. Therefore, based on the frequency change mount, the temperature of the measurement subject 20 can be measured.

A calculation of the phase change amount and a calculation of the strain of the measurement subject 20 from the phase change amount are implemented by a calculation circuit not shown as a strain amount calculation portion. A calculation of the resonant frequency change amount and a calculation of the temperature from the resonant frequency change amount are implemented by a calculation circuit not shown as a temperature calculation portion.

A measurement principle of the strain and the temperature of the sensor according to the first embodiment will be described.

Figure 2:
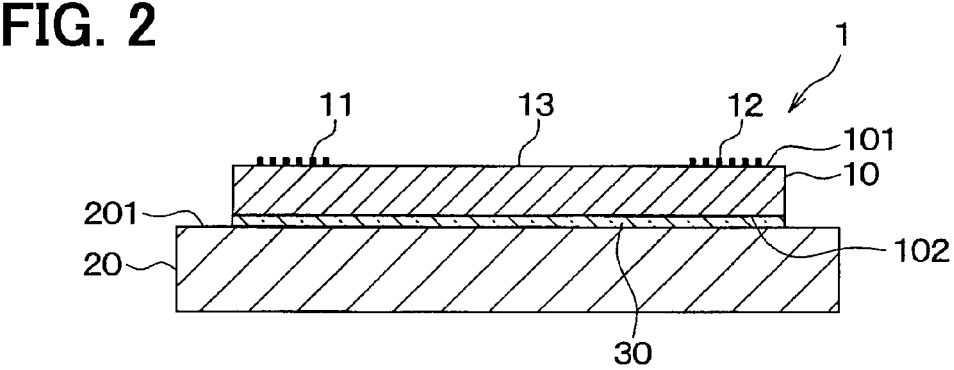
FIG. 2 is a sectional view showing a SAW device according to a first comparison example.
Figures 4A, 4B:
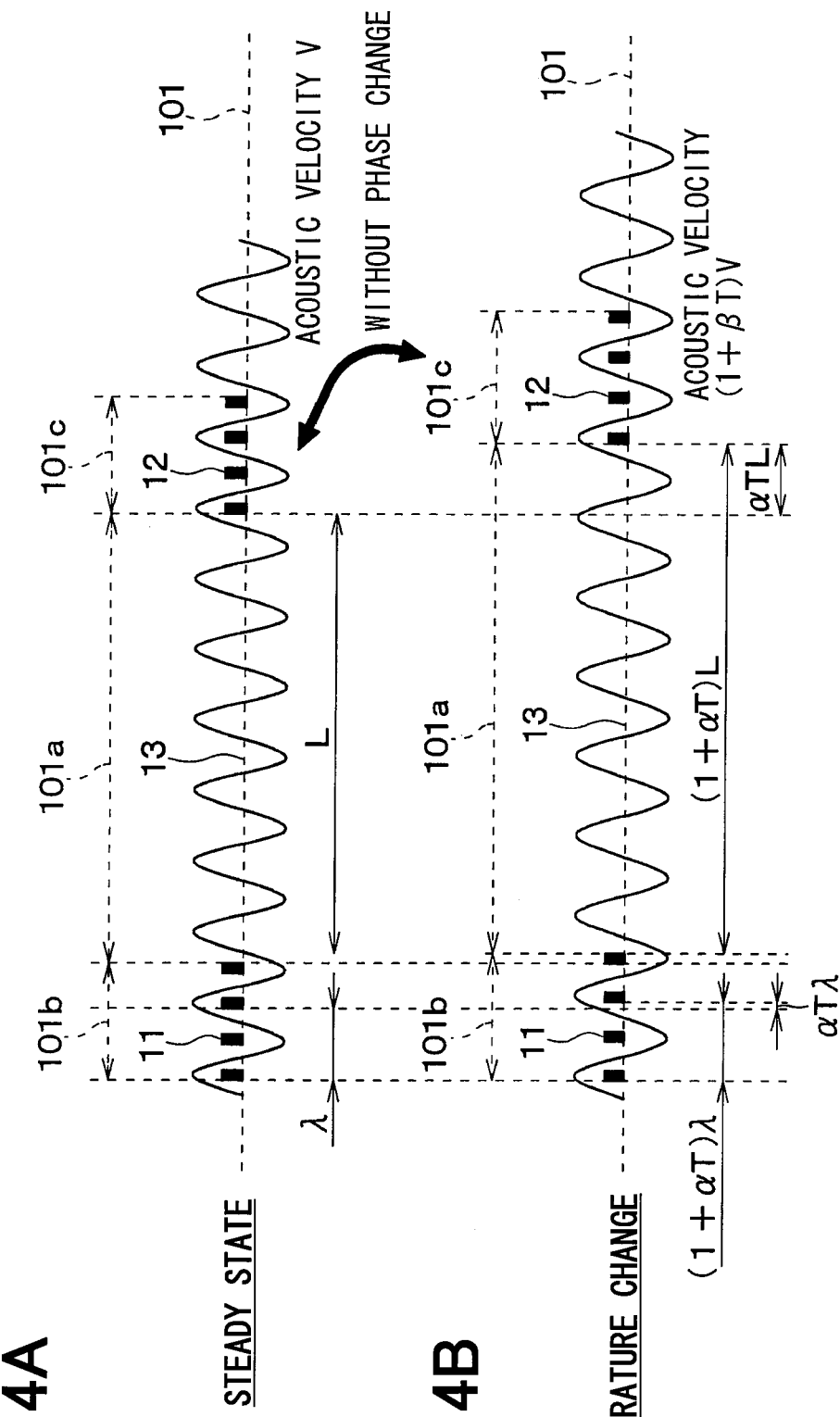
FIG. 4A is a schematic diagram showing a SAW of the SAW device in a steady state.
FIG. 4B is a schematic diagram showing a SAW of the SAW device in a temperature change state of the substrate, according to the first comparison example.

FIG. 2 is a sectional view showing the SAW device and the measurement subject 20 in the sensor according to a first comparison example. FIG. 3A is a schematic diagram showing the SAW of the SAW device 1 transmitted through the top surface 101 of the substrate 10 in a steady state according to the first comparison example. FIG. 3B is a schematic diagram showing the SAW of the SAW device 1 transmitted through the top surface 101 of the substrate 10 in a strain state of an entire substrate, according to the first comparison example. FIG. 4A is a schematic diagram showing the SAW of the SAW device 1 transmitted through the top surface 101 of the substrate 10 in a steady state according to the first comparison example.

FIG. 4B is a schematic diagram showing the SAW of the SAW device 1 transmitted through the top surface 101 of the substrate 10 in a temperature change state of the substrate 10, according to the first comparison example.

As shown in FIG. 2, in the sensor of the first comparison example, the whole bottom surface 102 of the substrate 10 in the SAW device 1 is fixed to the surface 201 of the measurement subject 20.

As shown in FIGS. 3A and 3B, when the strain of the measurement subject 20 is transmitted to the SAW device 1 of the first comparison, a strain is generated equally on the whole area of an area 101b, an area 101a, and an area 101c. The area 101b is an area where the drive electrode 11 of the top surface 101 of the substrate 10 is arranged at. The area 101a is an area where the propagation portion 13 of the top surface 101 of the substrate 10 is arranged at. The area 101c is an area where the reflector 12 of the top surface 101 of the substrate 10 is arranged at. Therefore, as shown in formulas (1) and (2), the phase of the SAW reached to the reflector 12 is not changed, comparing to the steady state.

As shown in FIG. 3A, when the SAW is in the steady state, the phase θ of the SAW reached to the reflector 12 is set based on a value after the decimal point as shown in formula (1). The value equals to a length L of the propagation portion 13 divided by a wavelength λ.

$$\theta = \mathrm{mod}\left(\frac{L}{\lambda}\right) \times 360 \qquad (1)$$

The phase θ is the phase of the SAW measured at a position of the reflector 12. The unit of the phase θ is deg. The wavelength λ, is a wavelength of the excited SAW. The unit of the wavelength λ is m. The length L is the length of the propagation portion 13. The unit of the length L is m.

As shown in FIG. 3B, when the strain is generated equally in the whole area of the top surface 101 of the substrate 10, and when the temperature change is not generated in the substrate 10, the wavelength of the SAW and the length of the propagation portion are changed by a same change rate ε. Therefore, as shown in formula (2), the phase θ of the SAW reached to the reflector 12 is not changed.

$$\theta = \mathrm{mod}\left(\frac{(1+\varepsilon)L}{(1+\varepsilon)\lambda}\right) \times 360 \qquad (2)$$

The change rate ε is a change rate according to the strain.

As shown in FIGS. 4A and 4B, when the temperature change is generated in the SAW device 1 of the first comparison example, a strain according to the temperature change is generated equally in the whole area of the area 101b, the area 101a, and the area 101c. Therefore, as shown in formulas (3), (4) and (5), the resonant frequency of the SAW excited by the drive electrode 11 is changed, but the phase of the SAW reached to the reflector 12 is not changed, comparing to the steady state.

As shown in FIG. 4A, when the SAW is in the steady state, the resonant frequency f of the SAW excited by the drive electrode 11 is set based on both an acoustic velocity V and the wavelength λ as shown in formula (3).

$$f = \frac{V}{\lambda} \qquad (3)$$

The frequency f is the resonant frequency of the SAW excited by the drive electrode 11. The unit of the frequency f is Hz. The velocity V is the acoustic velocity (propagation velocity of the SAW). The unit of the velocity V is m/s.

As shown in FIG. 4B, when the temperature change is generated in the substrate 10, and when the strain is not generated in the substrate 10, the acoustic velocity and the wavelength are respectively changed. As shown in formula (4), the resonant frequency f is changed. On the other hand, as shown in formula (5), the phase θ of the SAW reached to the reflector 12 is not changed because the phase θ is not affected by the acoustic velocity.

$$f(T) = \frac{(1+\beta T)L}{(1+\alpha T)\lambda} \qquad (4)$$

$$\theta = \mathrm{mod}\left(\frac{(1+\alpha T)L}{(1+\alpha T)\lambda}\right) \times 360 \qquad (5)$$

The temperature T is the temperature of the substrate 10. The unit of the temperature T is ° C. The coefficient α is a linear expansion coefficient of the substrate 10. The unit of the coefficient α is ppm/° C. The coefficient β is a temperature characteristic of the propagation velocity of the SAW. The unit of the coefficient β is ppm/° C.

Figure 5A:
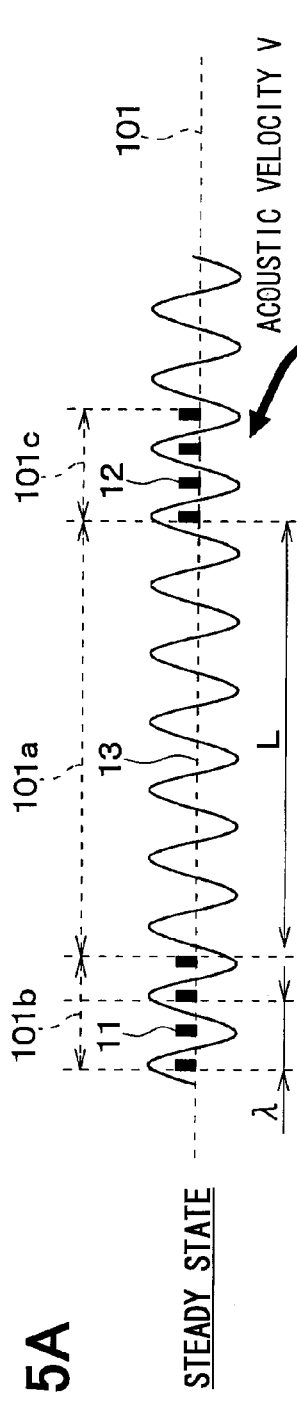
FIG. 5A is a schematic diagram showing a SAW of the SAW device in a steady state.
Figure 5B:
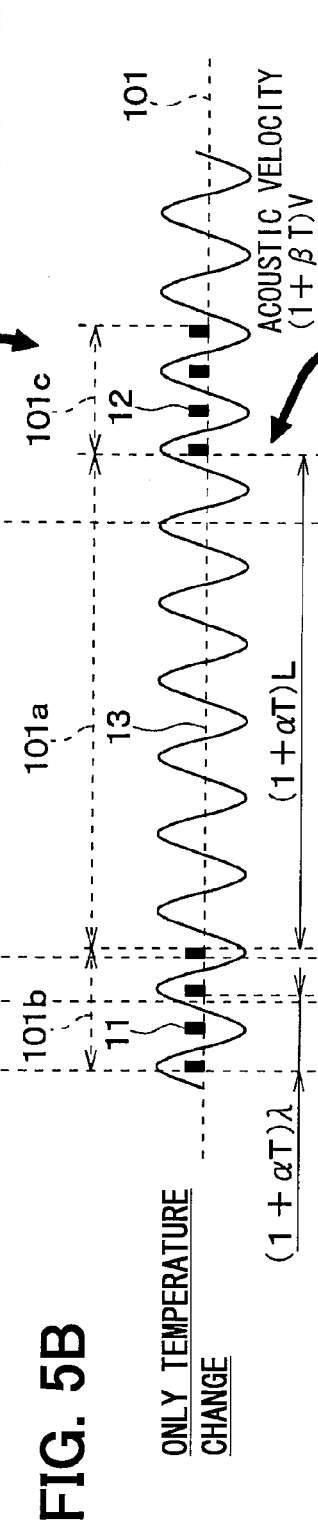
FIG. 5B is a schematic diagram showing a SAW of the SAW device in a temperature change state of a substrate.
Figure 5C:
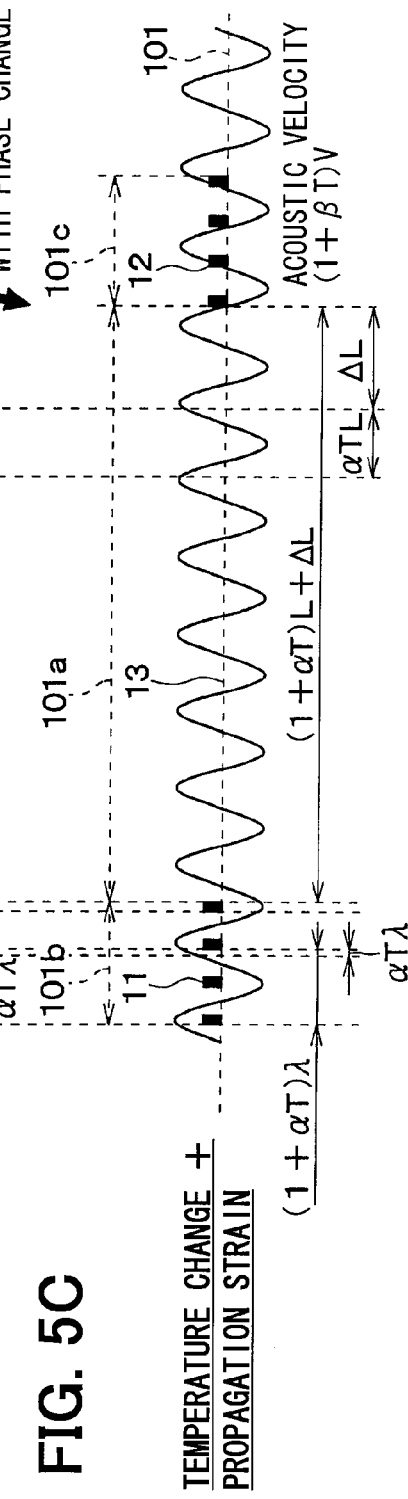
FIG. 5C is a schematic diagram showing a SAW of the SAW device in a state where a temperature change and a strain of a propagation direction are generated, according to the first embodiment.

FIG. 5A is a schematic diagram showing the SAW of the SAW device 1 transmitted through the top surface 101 of the substrate 10 in a steady state according to the first embodiment. FIG. 5B is a schematic diagram showing the SAW of the SAW device 1 transmitted through the top surface 101 of the substrate 10 in a temperature change state of the substrate 10, according to the first embodiment. FIG. 5C is a schematic diagram showing the SAW of the SAW device 1 transmitted through the top surface 101 of the substrate 10 in a state where the temperature change and the strain of a propagation direction are generated, according to the first embodiment.

As shown in FIGS. 5A and 5B, the sensor of the first embodiment, when the temperature change is generated in the substrate 10, and when the strain is not generated in the substrate 10, comparing to the steady state of the SAW, a same conclusion as the first comparison example is obtained as shown in formulas (4) and (5). That is, the resonant frequency of the SAW excited by the drive electrode 11 is changed, but the phase of the SAW reached to the reflector 12 is not changed because the phase is not affected by the acoustic velocity.

However, as shown in FIG. 5C, when the temperature change is generated in the substrate 10, and when the strain of the measurement subject 20 is transmitted to the substrate 10, the strain is generated only in the area 101a among the area 101b, the area 101a, and the area 101c. As shown in formula (6), comparing to the steady state of the SAW, the phase θ(T, ΔL) of the SAW reached to the reflector 12 is changed. The phase change amount Δθ(T, ΔL) is set according to the following formula (7).

$$\theta(T, \Delta L) = \mathrm{mod}\left(\frac{(1+\alpha T)L + \Delta L}{(1+\alpha T)\lambda}\right) \times 360 \quad (6)$$

$$\Delta\theta(T, \Delta L) = \mathrm{mod}\left(\frac{\Delta L}{(1+\alpha T)\lambda}\right) \times 360 \quad (7)$$

The phase change amount Δθ is the phase change amount of the SAW measured at the position of the reflector 12. The unit of the phase change amount Δθ is deg. The length change amount ΔL is a length change amount of the propagation portion 13 according to the strain. The unit of the length change amount ΔL is m.

As shown in formula (7), the temperature T is included in the phase change amount Δθ(T, ΔL) of the SAW. In a typical piezoelectric material such as LiNbO3, the coefficient α is 15.4 ppm/° C. Thus, an affect of the temperature T is extremely smaller than 1, that is, an error of calculating the strain of the measurement subject 20 from the phase change amount of the SAW is extremely small. Therefore, it can be said that the temperature change is hardly affected in the phase change amount of the SAW.

Therefore, by using the single SAW device 1, the strain of the measurement subject 20 can be measured based on the phase change of the SAW.

When the temperature change is generated in the substrate 10 in a case where the strain is generated only in the propagation portion 13, the resonant frequency is not affected by the strain of the propagation 13 as shown in formula (4). The temperature of the measurement subject 20 can be measured based on the resonant frequency change of the single SAW device 1.

When the strain is generated in the drive electrode 11, an electrode interval of the drive electrode 11 is changed, and the resonant frequency is changed. However, in the sensor of the first embodiment, the strain of the measurement subject 20 is not transmitted to the drive electrode 11 and the reflector 12. Therefore, the resonant frequency of the SAW device 1 is changed according to the temperature change, but is not affected by the strain.

As the above reasons, in the sensor of the first embodiment, both the strain and the temperature can be measured by using the single SAW device 1.

In FIG. 1B, a part of the area 102a placed at the bottom surface 102 directly under the propagation portion 13 is fixed to the measurement subject 20. The strain is not transmitted to the drive electrode 11 and the reflector 12, but only transmitted to the propagation portion 13. Therefore, as shown in FIG. 1B, it may be configured that at least a part of the area 102a is fixed to the measurement subject 20, and the whole area of both the area 102b and the area 102c is not fixed to the measurement subject 20.

(Second Embodiment)

Figure 6A:
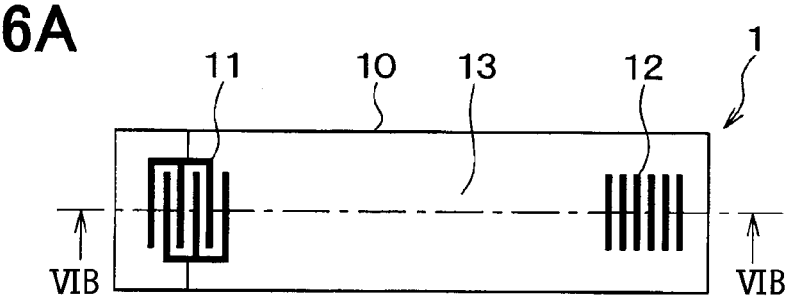
FIG. 6A is a schematic diagram showing a SAW device according to a second embodiment of the present disclosure.
Figure 6B:
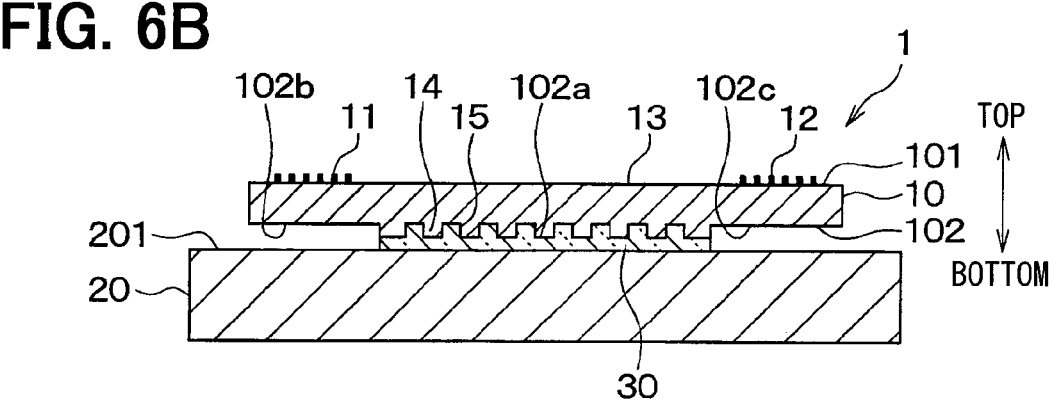
FIG. 6B is a sectional view taken along the line VIB-VIB of the SAW device in FIG. 6A.

FIG. 6A is a schematic diagram showing a SAW device 1 according to a second embodiment, and FIG. 6B is a sectional view taken along the line VIB-VIB in FIG. 6A.

In the second embodiment, with respect to the SAW device 1 shown in FIG. 1B according to the first embodiment, there is a different point that a plurality of convex portions 14 and a plurality of concave portions 15 are provided in a bonding surface 102a (area 102a) of the substrate 10 as shown in FIG. 6B. Hereafter, the different point which is different from the first embodiment will be mainly described.

Specifically, on the area 102a placed at the bottom surface 102 directly under the propagation portion 13, the plurality of the convex portions 14 and the plurality of the concave portions 15 are formed alternately. The plurality of the concave portions 15 may be formed by etching the area 102a such that the plurality of the convex portions 14 and the plurality of the concave portions 15 are formed.

A manufacturing process can be simplified by performing the etching for forming the plurality of the concave portions 15, and the etching for forming the areas 102b, 102c placed at the bottom surface 102 directly under the drive electrode 11 and the reflector 12 to be more recessed than the area 102a, at the same time.

Because the plurality of the convex portions 14 and the plurality of the concave portions 15 are provided in the bonding surface 102a of the substrate 10, a bonding size of the bonding surface 102a can be enlarged, and a bonding strength can be improved.

The other parts of the second embodiment may be the same as the first embodiment.

(Third Embodiment)

Figure 7A:
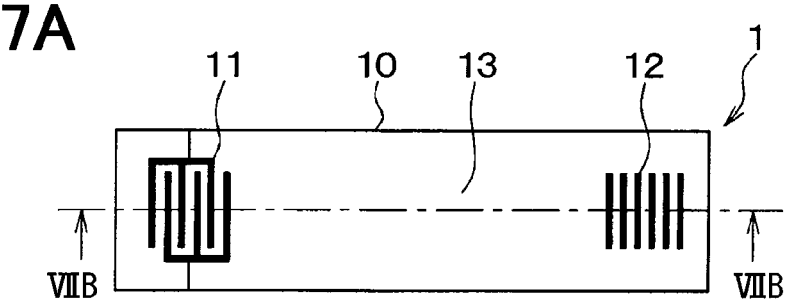
FIG. 7A is a schematic diagram showing a SAW device according to a third embodiment of the present disclosure.
Figure 7B:
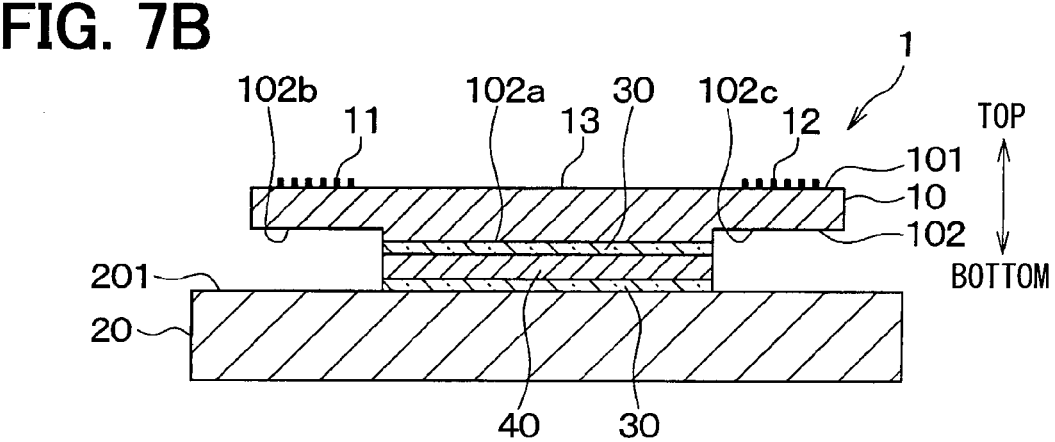
FIG. 7B is a sectional view taken along the line VIIB-VIIB of the SAW device in FIG. 7A.

FIG. 7A is a schematic diagram showing a SAW device 1 according to a third embodiment, and FIG. 7B is a sectional view taken along the line VIIB-VIIB in FIG. 7A.

In the third embodiment, with respect to the SAW device 1 shown in FIG. 1B according to the first embodiment, there is a different point that an insert member is arranged at a joint portion between the substrate 10 and the measurement subject 20 as shown in FIG. 7B. Hereafter, the different point which is different from the first embodiment will be mainly described.

Specifically, a metal plate 40 is arranged between the area 102a placed at the bottom surface 102 directly under the propagation portion 13 and the surface 201 of the measurement subject 20. By using the bonding material 30, the metal plate 40 is respectively bonded to the substrate 10 and the measurement subject 20.

The metal plate 40 has a thermal expansion coefficient between the substrate 10 and the measurement subject 20. For example, when the substrate 10 is made of a LiNbO3 (15.4 ppm/° C.), and when the measurement subject 20 is made of a SUS304 (17.3 ppm/° C.), the metal plate 40 may be made of such as a copper (16.5 ppm/° C.), or an 18-8 chrome nickel steel (16.7 ppm/° C.).

When a thermal expansion coefficient difference between the substrate 10 and the measurement subject 20 is large, a strain is generated in the joint portion between the substrate 10 and the measurement subject 20 by the temperature change being repeated, and thereby the substrate 10 and the measurement subject 20 are easily separated. However, in the third embodiment, the strain generated in the joint portion between the substrate 10 and the measurement subject 20 can be reduced, and a bonding between the substrate 10 and the measurement subject 20 can be maintained.

The other parts of the third embodiment may be the same as the second embodiment.

(Fourth Embodiment)

Figure 8A:
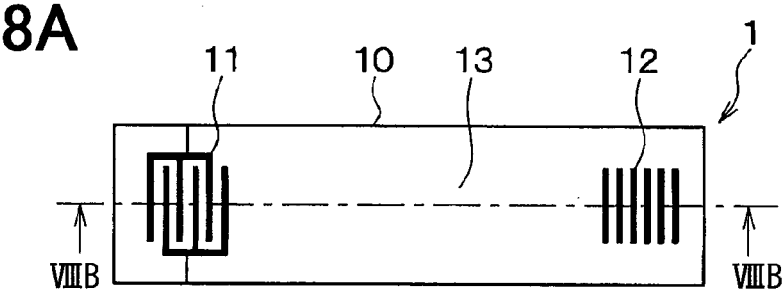
FIG. 8A is a schematic diagram showing a SAW device according to a fourth embodiment of the present disclosure.
Figure 8B:
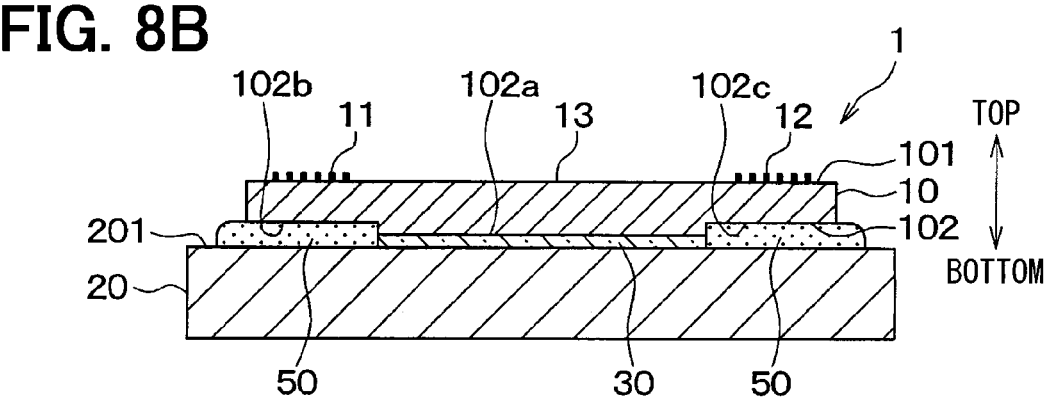
FIG. 8B is a sectional view taken along the line VIIIB-VIIIB of the SAW device in FIG. 8A.

FIG. 8A is a schematic diagram showing a SAW device 1 according to a fourth embodiment, and FIG. 8B is a sectional view taken along the line VIIIB-VIIIB in FIG. 8A.

In the fourth embodiment, with respect to the SAW device 1 shown in FIG. 1B according to the first embodiment, a gel-shaped member 50 is arranged between the areas 102b, 102c and the surface 201 of the measurement subject 20 as shown in FIG. 8B. Besides, the areas 102b, 102c are placed at the bottom surface 102 directly under the drive electrode (comb electrode) 11 and the reflector 12.

As the first embodiment, there may be a space between the areas 102b, 102c and the surface 201 of the measurement subject 20. When a vertical vibration of a specified frequency is transmitted to the SAW device 1, a sympathetic vibration may be generated because the area where the comb electrode 11 and the reflector 12 are arranged at is configured with a cantilever structure. By the sympathetic vibration, a tremor may be generated in the substrate 10, and thereby a malfunction may be generated, such that the substrate 10 may be damaged, or the substrate 10 and the measurement subject 20 may be separated.

In contrast, according to the fourth embodiment, by the gel-shaped member 50, the tremor generated in the area where the comb electrode 11 and the reflector 12 are arranged at can be restricted, and the malfunction from the tremor can be restricted.

When the strain is generated in the measurement subject 20, the gel-shaped member 50 is deformed. The strain of the measurement subject 20 is not transmitted to the comb electrode 11 and the reflector 12, but only transmitted to the propagation portion 13. Therefore, the strain of the measurement subject 20 can be measured. The gel-shaped member 50 may adhere to the substrate 10. In addition, the gel-shaped member 50 may be injected between the SAW device 1 and the measurement subject 20 after the SAW device 1 and the measurement subject 20 being bonded.

The other parts of the fourth embodiment may be the same as the first embodiment.

(Fifth Embodiment)

Figure 9A:
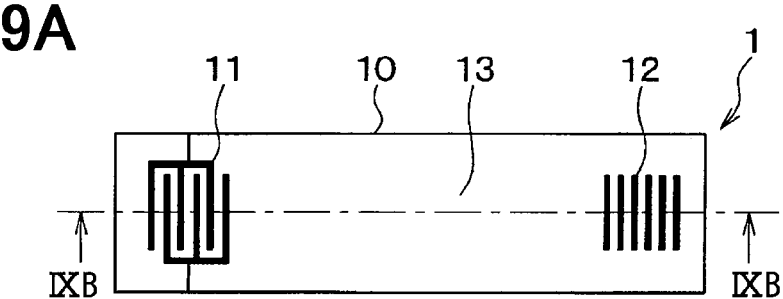
FIG. 9A is a schematic diagram showing a SAW device according to a fifth embodiment of the present disclosure.
Figure 9B:
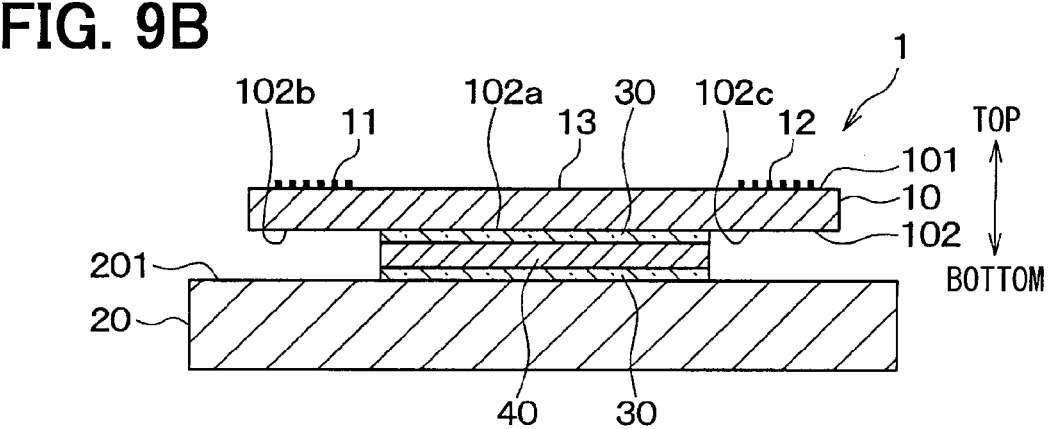
FIG. 9B is a sectional view taken along the line IXB-IXB of the SAW device in FIG. 9A.

FIG. 9A is a schematic diagram showing a SAW device 1 according to a fifth embodiment, and FIG. 9B is a sectional view taken along the line IXB-IXB in FIG. 9A.

In the first embodiment, a structure, in which only the area 102a placed at the bottom surface 102 directly under the propagation portion 13 is fixed to the surface 201 of the measurement subject 20, is obtained by the shape of the substrate 10. In the fifth embodiment, the structure is obtained by arranging an insert member between the substrate 10 and the measurement subject 20. Hereafter, a different point which is different from the first embodiment will be mainly described.

Specifically, as shown in FIG. 9B, the whole area of the bottom surface 102 of the substrate 10 is a flat surface. The whole area of the surface 201 of the measurement subject 20 face to the substrate 10 is also a flat surface. A metal plate 40 of a specified thickness is arranged between the area 102a and the surface 201 of the measurement subject 20. By using a bonding material 30, the metal plate 40 is respectively bonded to the substrate 10 and the measurement subject 20.

A size of the metal plate 40 in a direction parallel to the bottom surface 102 of the substrate 10 is smaller than or equal to a size of the area 102a. Therefore, a space is formed between the areas 102b, 102c and the surface 201 of the measurement subject 20. Besides, the areas 102b, 102c are placed at the bottom surface 102 directly under the comb electrode 11 and the reflector 12.

According to the fifth embodiment, both the substrate 10 and the measurement subject 20 may be not processed, that is, the metal plate 40 may add to a conventional mounting structure of both the SAW device 1 and the measurement subject 20. Comparing to mounting the substrate 10 and the measurement subject 20 after one of the substrate 10 and the measurement subject 20 being processed, a cost of the mounting can be reduced.

As the same as the metal plate 40 in the third embodiment, the metal plate 40 has a thermal expansion coefficient between the substrate 10 and the measurement subject 20. Therefore, the strain generated in the joint portion due to a thermal expansion coefficient difference between the substrate 10 and the measurement subject 20 can be reduced, and the bonding can be maintained.

In the fifth embodiment, the metal plate 40 is used as the insert member. At a point of view to obtain the structure that only the area 102a is fixed to the surface 201 of the measurement subject 20, the insert member may be made of materials except metal.

The other parts of the fifth embodiment may be the same as the first embodiment.

(Sixth Embodiment)

Figure 10A:
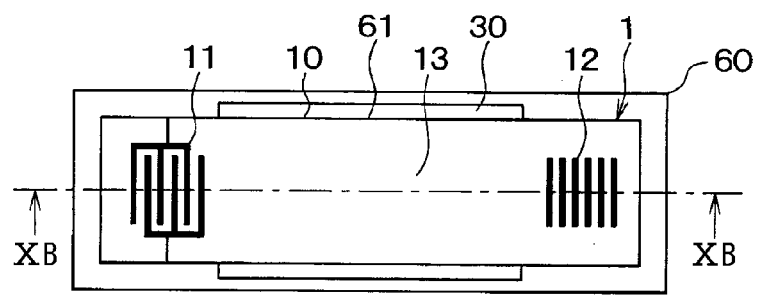
FIG. 10A is a schematic diagram showing a SAW device according to a sixth embodiment of the present disclosure.
Figure 10B:
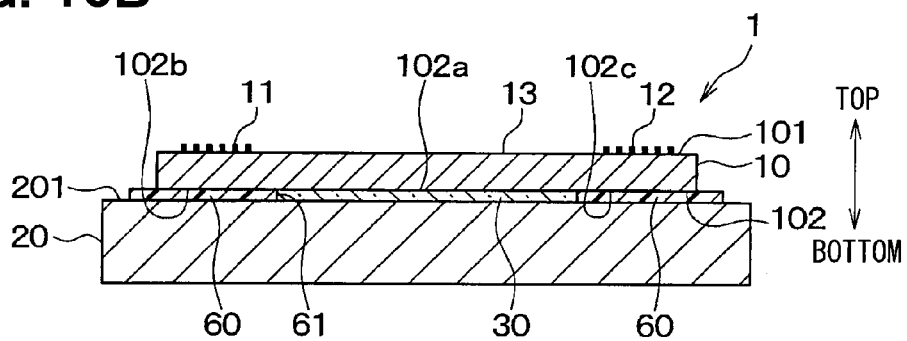
FIG. 10B is a sectional view taken along the line XB-XB of the SAW device in FIG. 10A.

FIG. 10A is a schematic diagram showing the SAW device 1 according to a sixth embodiment, and FIG. 10B is a sectional view taken along the line XB-XB in FIG. 10A.

In the sixth embodiment, the structure, in which only the area 102a placed at the bottom surface 102 directly under the propagation portion 13 is fixed to the surface 201 of the measurement subject 20, is obtained by using a non-bonding material. The non-bonding material is not bonded to the substrate 10 and the measurement subject 20. Hereafter, a different point which is different from the first embodiment will be mainly described.

As shown in FIGS. 10A and 10B, a lubrication sheet 60, as the non-bonding material, is arranged between the bottom surface 102 of the substrate 10 and the surface 201 of the measurement subject 20. The lubrication sheet 60 is a smooth sheet, for example, a sheet from Teflon (registered trademark).

The lubrication sheet 60 includes an opening portion 61. The opening portion 61 only faces to the area 102a. The bonding material 30 is arranged at the opening portion 61 of the lubrication sheet 60. Only the area 102a is bonded to the measurement subject 20 by the bonding material 30.

On the other hand, because the lubrication sheet 60 is arranged between the areas 102b, 102c and the measurement subject 20, the areas 102b, 102c are not bonded to the measurement subject 20. Besides, the areas 102b, 102c are placed at the bottom surface 102 directly under the comb electrode 11 and the reflector 12.

In the sixth embodiment, for example, the lubrication sheet 60 is arranged at the surface 201 of the measurement subject 20, and the bonding material 30 is applied to the opening portion 61 of the lubrication sheet 60. Then, the measurement subject 20 and the SAW device 1 are bonded by mounting the SAW device 1 on the surface 201 of the measurement subject 20.

According to the sixth embodiment, even if both the substrate 10 and the measurement subject 20 are not processed, the mounting of the SAW device 1 and the measurement subject 20 is implemented only by using the lubrication sheet 60. Comparing to mounting the substrate 10 and the measurement subject 20 after one of the substrate 10 and the measurement subject 20 being processed, a cost of the mounting can be reduced.

The lubrication sheet 60 may be removed after bonding the substrate 10 and the measurement subject 20, or may be remained after bonding the substrate 10 and the measurement subject 20 instead of being removed.

When the lubrication sheet 60 is removed after bonding the substrate 10 and the measurement subject 20, the lubrication sheet 60 can be reused during a process of mounting the substrate 10 and the measurement subject 20. Therefore, a mounting cost can be further reduced.

On the other hand, when the lubrication sheet 60 is not removed after bonding the substrate 10 and the measurement subject 20, the mounting structure is formed such that the lubrication sheet 60 is arranged between the areas 102b, 102c and the measurement subject 20. Thus, comparing to the case that the space is formed between the areas 102b, 102c and the surface 201 of the measurement subject 20, the tremor generated on the area of the substrate 10 where the comb electrode 11 and the reflector 12 are arranged at can be restricted similarly to the fourth embodiment.

(Seventh Embodiment)

Figure 11A:
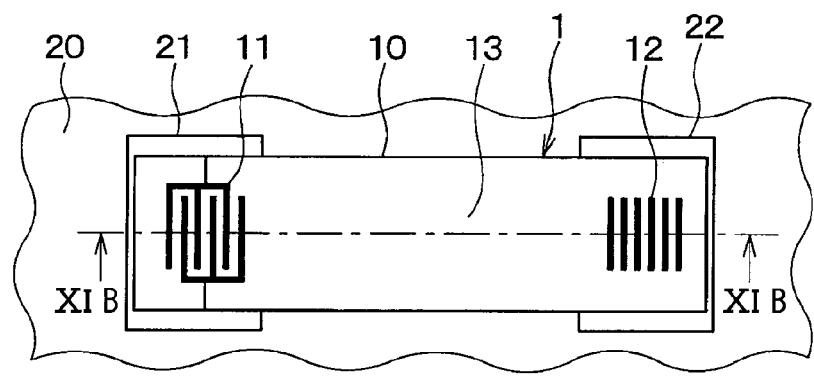
FIG. 11A is a schematic diagram showing a SAW device according to a seventh embodiment of the present disclosure.
Figure 11B:
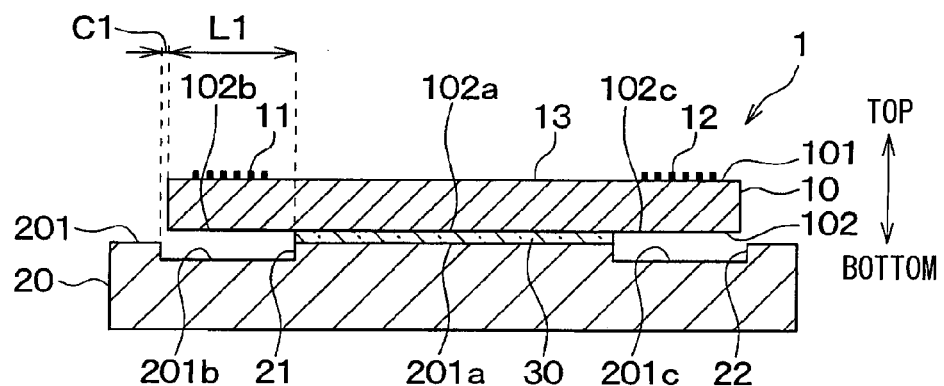
FIG. 11B is a sectional view taken along the line XIB-XIB of the SAW device in FIG. 11A.

FIG. 11A is a schematic diagram showing a SAW device 1 according to a seventh embodiment, and FIG. 11B is a sectional view taken along the line XIB-XIB in FIG. 11A.

In the seventh embodiment, the structure, in which only the area 102a placed at the bottom surface 102 directly under the propagation portion 13 is fixed to the surface 201 of the measurement subject 20, is obtained by a shape of the measurement subject 20. Hereafter, a different point which is different from the first embodiment will be mainly described.

As shown in FIGS. 11A, 11B, the measurement subject 20 is shaped such that two areas 201b, 201c placed at the surface 201 directly under the comb electrode 11 and the reflector 12 are more recessed than an area 201a placed at the surface 201 directly under the propagation portion 13.

The above shape of the measurement subject 20 can be obtained by forming two concave portions 21, 22 on the surface 201 of the measurement subject 20. The concave portions 21, 22 are formed by drilling the areas 201b, 201c.

The area 201a is bonded to the bottom surface 102 of the substrate 10 by the bonding material 30.

On the other hand, the areas 201b, 201c face to the areas 102b, 102c placed at the bottom surface 102 directly under the comb electrode 11 and the reflector 12, respectively, via a space. The whole area of the bottom surface 102 of the substrate 10 is a flat surface.

In the seventh embodiment, because of the shape of the measurement subject 20, the structure, in which only the area 102a is fixed to the surface 201 of the measurement subject 20, can be obtained without adding any other parts.

Comparing to processing the substrate 10 of the small SAW device 1, according to the seventh embodiment, it is easier to process the surface 201 of the measurement subject 20 which is larger than the SAW device 1.

According to the seventh embodiment, the areas 201b, 201c are formed to have the concave portions 21, 22. As shown in FIG. 11A, the concave portions 21, 22 are used as marks for showing a mounting position of the SAW device 1. Therefore, it is easy to mount the SAW device 1 to the measurement subject 20. It is preferable that two outer end portions are respectively placed at a position just or far from two end portions of the substrate 10 in a propagation direction of the SAW with respect to the area 102a. The outer end portions are two end portions of the concave portions 21, 22 far from the area 201a in the left-right direction with respect to the other two end portions of the concave portions 21, 22. The propagation direction of the SAW is a left-right direction shown in FIGS. 11A, 11B.

As shown in FIG. 11B, at a point of view to restrict an interfere between the substrate 10 and the measurement subject 20 when the substrate 10 is expanded, it is preferable that a clearance C1 is provided. The clearance C1 is set based on a proper temperature range, the thermal expansion coefficient difference between the substrate 10 and the measurement subject 20, and a distance L1. The distance L1 may be a distance of one of the areas 102b, 102c in the left-right direction.

(Eighth Embodiment)

Figure 12A:
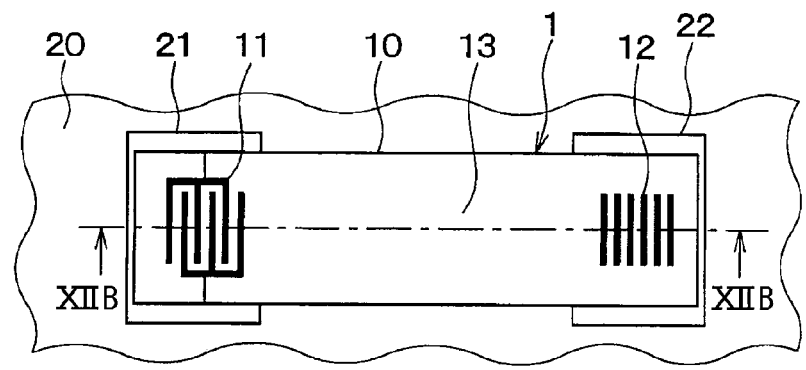
FIG. 12A is a schematic diagram showing a SAW device according to an eighth embodiment of the present disclosure.
Figure 12B:
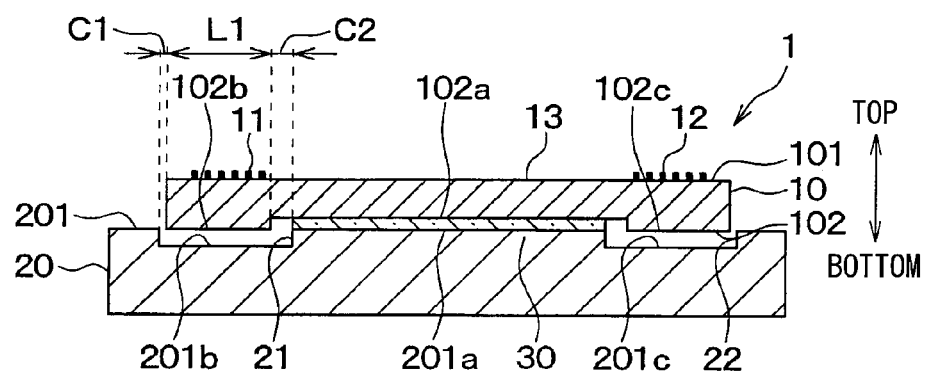
FIG. 12B is a sectional view taken along the line XIIB-XIIB of the SAW device in FIG. 12A.

FIG. 12A is a schematic diagram showing a SAW device 1 according to an eighth embodiment, and FIG. 12B is a sectional view taken along the line XIIB-XIIB in FIG. 12A.

In the eighth embodiment, as shown in FIG. 12B, the shape of the substrate 10 is further changed with respect to the SAW device 1 of the seventh embodiment shown in FIG. 11B.

Specifically, on the substrate 10 of the SAW device 1, the areas 102b, 102c are more protruded toward the measurement subject 20, than the area 102a. Besides, the area 102a is placed at the bottom surface 102 directly under the propagation portion 13, and the areas 102b, 102c are placed at the bottom surface 102 directly under the comb electrode 11 and the reflector 12.

The above shape of the substrate 10 is formed by etching the area 102a. Besides, a depth of the area 102a is smaller than a depth of the concave portions 21, 22 of the measurement subject 20.

Therefore, according to the eighth embodiment, when the SAW device 1 is mounted to the measurement subject 20, two convex portions 102b, 102c on the bottom surface 102 of the substrate 10 are inserted into the concave portions 21, 22 on the surface 201 of the measurement subject 20. Because a position of the SAW device 1 with respect to the measurement subject 20 is fixed, it is easy to mount the SAW device 1 to the measurement subject 20.

In the eighth embodiment, as shown in FIG. 12B, at the point of view to restrict the interfere between the substrate 10 and the measurement subject 20 when the substrate 10 is expanded, it is preferable that two clearances C1, C2 are provided. The clearances C1, C2 are set based on the proper temperature range, the thermal expansion coefficient difference between the substrate 10 and the measurement subject 20, and the distance L1. The distance L1 may be a distance of one of the areas 102*b*, 102*c* in the left-right direction.

(Ninth Embodiment)

In a ninth embodiment, with respect to both the SAW device 1 and the measurement subject 20 described in the eighth embodiment, a convex-shape and a concave-shape are interchanged with each other.

That is, in contradiction to the measurement subject 20 shown in FIG. 12B, a measurement subject 20 (not shown) is shaped such that an area 201*a* is more recessed than two areas 201*b*, 201*c*.

On the other hand, in contradiction to the substrate 10 shown in FIG. 12B, in a substrate 10 of a SAW device 1 of the ninth embodiment, the areas 102*b*, 102*c* are more protruded than the area 102*a*. Besides, the area 102*a* is placed at the bottom surface 102 directly under the propagation portion 13, and the areas 102*b*, 102*c* are placed at the bottom surface 102 directly under the comb electrode 11 and the reflector 12.

As the same as the eighth embodiment, when the SAW device 1 is mounted to the measurement subject 20, a convex portion on the bottom surface 102 of the substrate 10 is inserted into a concave portion on the surface 201 of the measurement subject 20. Because a position of the SAW device 1 with respect to the measurement subject 20 is fixed, it is easy to mount the SAW device 1 to the measurement subject 20.

(Other Embodiment)

(1) In the above-described embodiments, the entire substrate 10 is made of the piezoelectric material. A part of the substrate 10 may be formed by the piezoelectric material so that a piezoelectric thin film formed by the piezoelectric material is arranged at the substrate 10.

(2) In the above-described embodiments, the SAW device 1 reflects the SAW by the reflector 12, and receives the reflected SAW by the comb electrode 11. A receiving electrode for receiving the SAW from the comb electrode 11 may be used instead of the reflector 12. In this case, the comb electrode 11 may correspond to a first electrode for oscillating the SAW, and the receiving electrode may correspond to a second electrode for receiving the SAW.

(3) The above-described embodiments may combine with each other within the scope of the present disclosure. For example, the gel-shaped member 50 used in the fourth embodiment may be arranged at the space between the areas 102*b*, 102*c* and the surface 201 of the measurement subject 20 in the above-described embodiments except the first and the fourth embodiments.

The above-described embodiments of the present disclosure may include technical aspects hereafter. According to a first aspect of the present disclosure, a surface acoustic wave sensor includes a substrate, a first electrode, a second electrode, a propagation portion, a phase detection device and a frequency detection device. The substrate is arranged at the surface of the measurement subject which is a measuring object of both the strain and the temperature. At least a part of the substrate may be made of the piezoelectric material. The first electrode is arranged at the top surface of the substrate. The first electrode oscillates or receives the SAW. The second electrode is arranged at the top surface of the substrate. The second electrode receives or reflects the SAW oscillated by the first electrode. The propagation portion is placed at the top surface of the substrate between the first electrode and the second electrode. The propagation portion transmits the SAW from the first electrode toward the second electrode. The phase detection device detects a phase of the SAW oscillated by the first electrode and a phase of the SAW received or reflected by the second electrode. The frequency detection device detects a resonant frequency of the first electrode.

A first area, which is placed at the bottom surface of the substrate directly under the propagation portion, is fixed to the measurement subject. A second area, which is placed at the bottom surface of the substrate directly under the first electrode and the second electrode, is not fixed to the measurement subject.

Between the areas of the bottom surface of the substrate placed directly under the first and the second electrodes and the propagation portion, only the first area placed directly under the propagation portion is bonded to the measurement subject. When the strain is generated in the measurement subject, the strain of the measurement subject is only transmitted to the propagation portion. Because the first area of the substrate fixed to the measurement subject is bonded to the measurement subject, the first area is deformed corresponding to a deformation of the measurement subject. Because the second area of the substrate not fixed to the measurement subject is not bonded to the measurement subject, the second area is not deformed.

Therefore, when the strain is generated in the measurement subject, the strain is generated only in the propagation portion, and thereby a phase change is generated in the SAW received or reflected by the second electrode with respect to a phase of the SAW oscillated by the first electrode. The phase change is hardly affected by a temperature change of the measurement subject, because a temperature change is generated equally in the first electrode, the second electrode and the propagation portion, when the temperature of the measurement subject is changed.

Thus, the strain of the measurement subject can be measured based on the phase change of the SAW detected by the phase detection device. Besides, the SAW is received or reflected by the second electrode.

When the temperature of the measurement subject is changed, an acoustic velocity of the SAW is changed. Because an interval between electrodes of the first electrode is expanded (contracted) by the temperature change, the resonant frequency of the first electrode is changed when the SAW is excited. When the strain is generated in the measurement subject, the strain is only generated in the propagation portion, and the strain of the propagation portion does not affect the resonant frequency. In this case, the resonant frequency change is not affected by the strain of the measurement subject.

The temperature of the measurement subject can be measured based on the resonant frequency change detected by the frequency detection device. Therefore, both the strain and the temperature can be measured by the single SAW device.

According to the second aspect of the present disclosure, the substrate may be shaped such that the second area is more recessed than the first area. The first area may be bonded to the measurement subject by the bonding material.

According to the third aspect of the present disclosure, in the substrate, a plurality of convex portions and a plurality of concave portions may be provided in the first area. The bonding strength between the substrate and the measurement subject can be improved.

According to the fourth aspect of the present disclosure, the measurement subject may be shaped such that the area placed at the surface of the measurement subject directly under the first and the second electrodes is more recessed than the area placed at the surface of the measurement subject directly under the propagation portion. The area placed at the surface of the measurement subject directly under the propagation may be bonded to the substrate by the bonding material.

Because the measurement subject is shaped as above, a structure for fixing the substrate and the measurement subject can be obtained.

According to the fifth aspect of the present disclosure, the substrate may be shaped such that the second area is more protruded than the first area. When the SAW device is mounted to the measurement subject, the SAW device may be arranged so that a convex portion on the bottom surface of the substrate can be inserted into a concave portion on the surface of the measurement subject. It is easy to decide a position for the SAW device with respect to the measurement subject.

According to the sixth aspect of the present disclosure, among areas placed at the bottom surface of the substrate directly under the first electrode, the second electrode and the propagation portion, the bonding material may be arranged between the first area and the measurement subject.

Because the bonding material is arranged at the first area, even though both the bottom surface of the substrate and the surface of the measurement subject are flat surfaces, a structure for fixing the substrate and the measurement subject can be obtained.

According to the seventh aspect of the present disclosure, a space may be formed between the second area and the measurement subject. Alternatively, a sheet-shaped non-bonding material, which is not bonded to the substrate or the measurement subject, may be arranged between the second area and the measurement subject.

According to the eighth aspect of the present disclosure, among the areas placed at the bottom surface of the substrate directly under the first electrode, the second electrode and the propagation portion, only the first area may be bonded to the insert member by the bonding material. Besides, the insert member may be bonded to the measurement subject by the bonding material.

By using the insert member, even though both the bottom surface of the substrate and the surface of the measurement subject are flat surfaces, a structure for fixing the substrate and the measurement can be obtained.

According to the ninth aspect of the present disclosure, a gel-shaped member may be arranged between the second area and the measurement subject.

Comparing to a case that a space is formed without arranging the gel-shaped member, a tremor of the substrate can be reduced, and the tremor generated in the area of the substrate where the first and the second electrodes are arranged at can be restricted. The malfunction of the substrate and the joint portion from the tremor can be restricted.

While the present disclosure has been described with reference to the embodiments thereof, it is to be understood that the disclosure is not limited to the embodiments and constructions. The present disclosure is intended to cover various modification and equivalent arrangements. In addition, while the various combinations and configurations, which are preferred, other combinations and configurations, including more, less or only a single element, are also within the spirit and scope of the present disclosure.

What is claimed is:

1. A surface acoustic wave sensor comprising:
   a substrate arranged at a surface of a measurement subject which is a measuring object of both a strain and a temperature, at least a part of the substrate being made of a piezoelectric material;
   a first electrode arranged at a top surface of the substrate to oscillate or receive a surface acoustic wave;
   a second electrode arranged at the top surface of the substrate to receive or reflect the surface acoustic wave oscillated by the first electrode;
   a propagation portion placed at the top surface of the substrate between the first electrode and the second the electrode to transmit the surface acoustic wave from the first electrode toward the second electrode;
   a phase detection device detecting a phase of the surface acoustic wave oscillated by the first electrode and a phase of the surface acoustic wave received or reflected by the second electrode; and
   a frequency detection device detecting a resonant frequency of the first electrode, wherein
   a first area placed at a bottom surface of the substrate directly under the propagation portion is fixed to the measurement subject, and a second area placed at the bottom of the substrate directly under both the first electrode and the second electrode is not fixed to the measurement subject.

2. A surface acoustic wave sensor according to claim 1, wherein
   the substrate is shaped such that the second area is more recessed than the first area, and
   the first area is bonded to the measurement subject by a bonding material.

3. A surface acoustic wave sensor according to claim 2, wherein
   a plurality of convex portions and a plurality of concave portions are provided in the first area.

4. A surface acoustic wave sensor according to claim 1, wherein
   the measurement subject is shaped such that an area placed at the surface of the measurement subject directly under both the first electrode and the second electrode is more recessed than an area placed at the surface of the measurement subject directly under the propagation portion, and
   the area placed at the surface of the measurement subject directly under the propagation portion is bonded to the substrate by a bonding material.

5. A surface acoustic wave sensor according to claim 4, wherein
   the substrate is shaped such that the second area is more protruded than the first area.

6. A surface acoustic wave sensor according to claim 1, wherein
   among the areas placed at the bottom surface of the substrate directly under the first electrode, the second electrode and the propagation portion, a bonding material is arranged between only the first area and the measurement subject.

7. A surface acoustic wave sensor according to claim 6, wherein
   a sheet-shape non-bonding material, which is not bonded to the substrate or the measurement subject, is arranged between the second area and the measurement subject.

8. A surface acoustic wave sensor according to claim 1, wherein
   among the areas placed at the bottom surface of the substrate directly under the first electrode, the second electrode and the propagation portion, only the first area is bonded to an insert member by a bonding material, and
   the insert member is bonded to the measurement subject by the bonding material.

9. A surface acoustic wave sensor according to claim 2, wherein
   a gel-shaped member is arranged between the second area and the measurement subject.

* * * * *